US010463286B2

(12) United States Patent
Schenkman et al.

(10) Patent No.: US 10,463,286 B2
(45) Date of Patent: *Nov. 5, 2019

(54) DETERMINATION OF TISSUE OXYGENATION IN VIVO

(71) Applicant: University of Washington through its Center for Commercialization, Seattle, WA (US)

(72) Inventors: Kenneth Schenkman, Seattle, WA (US); Lorilee Arakaki, Bainbridge Island, WA (US); Wayne Ciesielski, Seattle, WA (US); Jeremy Shaver, Shoreline, WA (US)

(73) Assignee: University of Washington, Seattle, WA (US)

( * ) Notice: Subject to any disclaimer, the term of this patent is extended or adjusted under 35 U.S.C. 154(b) by 346 days.

This patent is subject to a terminal disclaimer.

(21) Appl. No.: 15/430,334

(22) Filed: Feb. 10, 2017

(65) Prior Publication Data

US 2017/0150912 A1 Jun. 1, 2017

Related U.S. Application Data

(63) Continuation of application No. 13/883,279, filed as application No. PCT/US2011/059121 on Nov. 3, 2011, now Pat. No. 9,591,999.

(Continued)

(51) Int. Cl.
*A61B 5/1455* (2006.01)
*A61B 5/00* (2006.01)
(Continued)

(52) U.S. Cl.
CPC ........ *A61B 5/14552* (2013.01); *A61B 5/1455* (2013.01); *A61B 5/14546* (2013.01);
(Continued)

(58) Field of Classification Search
CPC .............. A61B 5/1455; A61B 5/14551; A61B 5/14552; A61B 5/6801; A61B 5/72; A61B 5/7225; A61B 5/7271; A61B 2562/0233
See application file for complete search history.

(56) References Cited

U.S. PATENT DOCUMENTS 3,830,222 A 8/1974 Chance
4,281,645 A 8/1981 Jöbsis
(Continued)

FOREIGN PATENT DOCUMENTS

DE 69429426 T2 8/2002
DE 69627477 T2 3/2004
(Continued)

OTHER PUBLICATIONS

Aldridge, P.K., et al., "Identification of Tablet Formulations Inside Blister Packages by Near-Infrared Spectroscopy," Applied Spectroscopy 48(10):1272-1276, Oct. 1994.
(Continued)

*Primary Examiner* — Eric F Winakur
(74) *Attorney, Agent, or Firm* — Christensen O'Connor Johnson Kindness, PLLC; Ryan E. Dodge, Jr.

(57) ABSTRACT

A system and method for noninvasively determining the oxygenation of a tissue, for example, a muscle, in vivo uses optical methods to optically interrogate the tissue in both a visible wavelength range and a near infrared (NIR) wavelength range. The illuminating light is sculpted in intensity to approximately match the absorbance spectrum, for example, with the visible light having an intensity an order of magnitude greater than the NIR light. Training data is obtained from healthy patients in both the visible and NIR ranges simultaneously and used to calculate muscle oxygenation.

21 Claims, 4 Drawing Sheets

Related U.S. Application Data (60) Provisional application No. 61/409,793, filed on Nov. 3, 2010.

(51) Int. Cl.
*A61B 5/145* (2006.01)
*A61B 90/00* (2016.01)

(52) U.S. Cl.
CPC ........ *A61B 5/14551* (2013.01); *A61B 5/6801* (2013.01); *A61B 5/7271* (2013.01); *A61B 2090/3614* (2016.02); *A61B 2562/0238* (2013.01); *A61B 2562/043* (2013.01)

(56) References Cited

U.S. PATENT DOCUMENTS

| | | |
|---|---|---|
| 4,570,638 A | 2/1986 | Stoddart |
| 4,822,169 A | 4/1989 | Distl |
| 5,088,493 A | 2/1992 | Giannini |
| 5,119,815 A | 6/1992 | Chance |
| 5,190,039 A | 3/1993 | Takeuchi |
| 5,212,386 A | 5/1993 | Gratton |
| 5,217,013 A | 6/1993 | Lewis |
| 5,231,464 A | 7/1993 | Ichimura |
| 5,284,137 A | 2/1994 | Kessler |
| 5,323,010 A | 6/1994 | Gratton |
| 5,349,961 A | 9/1994 | Stoddart |
| 5,386,827 A | 2/1995 | Chance |
| 5,441,054 A | 8/1995 | Tsuchiya |
| 5,465,714 A | 11/1995 | Scheuing |
| 5,477,853 A | 12/1995 | Farkas |
| 5,482,034 A | 1/1996 | Lewis |
| 5,492,118 A | 2/1996 | Gratton |
| 5,517,987 A | 5/1996 | Tsuchiya |
| 5,564,417 A | 10/1996 | Chance |
| 5,584,296 A | 12/1996 | Cui |
| 5,628,310 A | 5/1997 | Rao |
| 5,694,931 A | 12/1997 | Tsuchiya |
| 5,769,791 A | 6/1998 | Benaron |
| 5,772,587 A | 6/1998 | Gratton |
| 5,772,597 A | 6/1998 | Goldberger |
| 5,779,631 A | 7/1998 | Chance |
| 5,795,292 A | 8/1998 | Lewis |
| 5,814,820 A | 9/1998 | Dong |
| 5,873,821 A | 2/1999 | Chance |
| 5,879,294 A | 3/1999 | Anderson |
| 5,902,235 A | 5/1999 | Lewis |
| 5,931,779 A | 8/1999 | Arakaki |
| 5,954,053 A | 9/1999 | Chance |
| 5,987,351 A | 11/1999 | Chance |
| 6,078,833 A | 6/2000 | Hueber |
| 6,134,460 A | 10/2000 | Chance |
| 6,161,031 A | 12/2000 | Hochman |
| 6,192,260 B1 | 2/2001 | Chance |
| 6,192,261 B1 | 2/2001 | Gratton |
| 6,216,021 B1 | 4/2001 | Franceschini |
| 6,263,221 B1 | 7/2001 | Chance |
| 6,304,767 B1 | 10/2001 | Soller |
| 6,377,840 B1 | 4/2002 | Gritsenko |
| 6,381,480 B1 | 4/2002 | Stoddart |
| 6,456,862 B2 | 9/2002 | Benni |
| 6,475,144 B1 | 11/2002 | Sah |
| 6,505,059 B1 | 1/2003 | Kollias |
| 6,526,309 B1 | 2/2003 | Chance |
| 6,549,795 B1 | 4/2003 | Chance |
| 6,564,076 B1 | 5/2003 | Chance |
| 6,564,088 B1 | 5/2003 | Soller |
| 6,615,065 B1 | 9/2003 | Barrett |
| 6,667,803 B1 | 12/2003 | Flessland |
| 6,687,620 B1 | 2/2004 | Haaland |
| 6,708,048 B1 | 3/2004 | Chance |
| 6,721,582 B2 | 4/2004 | Trepagnier |
| 6,785,568 B2 | 8/2004 | Chance |
| 6,794,659 B2 | 9/2004 | Barbieri |
| 6,859,658 B1 | 2/2005 | Krug |
| 7,047,054 B2 | 5/2006 | Benni |
| 7,113,814 B2 | 9/2006 | Ward |
| 7,130,672 B2 | 10/2006 | Pewzner |
| 7,221,969 B2 | 5/2007 | Stoddart |
| 7,239,901 B2 | 7/2007 | Gritsenko |
| 7,245,373 B2 | 7/2007 | Soller |
| 7,313,424 B2 | 12/2007 | Mayevsky |
| 7,313,427 B2 | 12/2007 | Benni |
| 7,355,688 B2 | 4/2008 | Lash |
| 7,515,948 B1 | 4/2009 | Balberg |
| 7,525,647 B2 | 4/2009 | Lash |
| 7,532,919 B2 | 5/2009 | Soyemi |
| 7,538,865 B2 | 5/2009 | Lash |
| 7,541,602 B2 | 6/2009 | Metzger |
| 7,613,489 B2 | 11/2009 | Myers |
| 7,616,303 B2 | 11/2009 | Yang |
| 7,881,892 B2 | 2/2011 | Soyemi |
| 8,126,527 B2 | 2/2012 | Marcinek |
| 2003/0032064 A1 | 2/2003 | Soller |
| 2003/0088163 A1 | 5/2003 | Soller |
| 2004/0005717 A1 | 1/2004 | Soller |
| 2004/0024297 A1 | 2/2004 | Chen |
| 2004/0111016 A1 | 6/2004 | Casscells, III |
| 2005/0059868 A1 | 3/2005 | Schurman |
| 2005/0094416 A1 | 5/2005 | Schmitz |
| 2005/0119541 A1 | 6/2005 | Lorenz |
| 2005/0186648 A1 | 8/2005 | Schurman |
| 2005/0277818 A1 | 12/2005 | Myers |
| 2005/0287548 A1 | 12/2005 | Bao |
| 2006/0122475 A1 | 6/2006 | Balberg |
| 2006/0189861 A1 | 8/2006 | Chen |
| 2006/0195024 A1 | 8/2006 | Benni |
| 2006/0247506 A1 | 11/2006 | Balberg |
| 2006/0256338 A1 | 11/2006 | Gratton |
| 2006/0276696 A1 | 12/2006 | Schurman |
| 2007/0051379 A1 | 3/2007 | Lash |
| 2007/0055119 A1 | 3/2007 | Lash |
| 2007/0112258 A1 | 5/2007 | Soyemi |
| 2007/0133984 A1 | 6/2007 | Maier |
| 2007/0265513 A1 | 11/2007 | Schenkman |
| 2008/0009689 A1 | 1/2008 | Benaron |
| 2008/0009748 A1 | 1/2008 | Gratton |
| 2008/0097173 A1 | 4/2008 | Soyemi |
| 2008/0106792 A1 | 5/2008 | Lash |
| 2008/0108886 A1 | 5/2008 | Lash |
| 2008/0200780 A1 | 8/2008 | Schenkman |
| 2008/0285029 A1 | 11/2008 | Benni |
| 2008/0287758 A1 | 11/2008 | Benaron |
| 2008/0300473 A1 | 12/2008 | Benni |
| 2008/0300474 A1 | 12/2008 | Benni |
| 2008/0304793 A1 | 12/2008 | Benaron |
| 2008/0312533 A1 | 12/2008 | Balberg |
| 2008/0316488 A1 | 12/2008 | Mao |
| 2009/0024013 A1 | 1/2009 | Soller |
| 2009/0048502 A1 | 2/2009 | Benaron |
| 2009/0108205 A1 | 4/2009 | Duffy |
| 2009/0182209 A1 | 7/2009 | Benni |
| 2009/0187086 A1 | 7/2009 | Benaron |
| 2009/0234209 A1 | 9/2009 | Lash |
| 2009/0259117 A1 | 10/2009 | Wider |
| 2009/0264722 A1 | 10/2009 | Metzger |
| 2009/0275812 A1 | 11/2009 | Reichgott |
| 2009/0281403 A1 | 11/2009 | Benni |
| 2009/0292187 A1 | 11/2009 | Mao |
| 2009/0326354 A1 | 12/2009 | Mao |
| 2010/0049018 A1 | 2/2010 | Duffy |
| 2010/0056887 A1 | 3/2010 | Kimura |
| 2010/0076319 A1 | 3/2010 | Mannheimer |
| 2010/0087718 A1 | 4/2010 | Gonopolskiy |
| 2010/0087719 A1 | 4/2010 | Benni |
| 2010/0105998 A1 | 4/2010 | Benni |
| 2010/0113900 A1 | 5/2010 | Shakespeare |
| 2010/0123897 A1 | 5/2010 | Yang |
| 2010/0177100 A1 | 7/2010 | Carnes |
| 2010/0198030 A1 | 8/2010 | Benaron |
| 2010/0210929 A1 | 8/2010 | Jossart |
| 2010/0222654 A1 | 9/2010 | Gonopolskiy |
| 2010/0301215 A1 | 12/2010 | Gonopolskiy |

(56) References Cited

U.S. PATENT DOCUMENTS

| | | |
|---|---|---|
| 2011/0028812 A1 | 2/2011 | Benni |
| 2011/0102791 A1 | 5/2011 | Johnson |
| 2011/0133086 A1 | 6/2011 | Benaron |

FOREIGN PATENT DOCUMENTS

| | | |
|---|---|---|
| DE | 69433205 T2 | 8/2004 |
| EP | 0 271 340 A1 | 6/1988 |
| EP | 0 441 791 B1 | 9/1997 |
| EP | 0 591 289 B1 | 7/1999 |
| EP | 1 080 683 A3 | 3/2001 |
| EP | 0 916 349 A3 | 7/2001 |
| EP | 0 808 124 B1 | 4/2003 |
| EP | 0 816 829 B1 | 8/2003 |
| EP | 1 181 530 B1 | 6/2005 |
| EP | 1 054 620 B1 | 1/2010 |
| EP | 2 289 415 A1 | 3/2011 |
| EP | 1 259 791 A2 | 11/2013 |
| EP | 1 885 235 B1 | 12/2013 |
| WO | 92/21283 A1 | 12/1992 |
| WO | 97/17013 A1 | 5/1997 |
| WO | 99/26528 A1 | 6/1999 |
| WO | 99/39630 A1 | 8/1999 |
| WO | 00/21435 A1 | 4/2000 |
| WO | 00/59374 A1 | 10/2000 |
| WO | 00/75635 A1 | 12/2000 |
| WO | 00/75638 A1 | 12/2000 |
| WO | 01/03598 A1 | 1/2001 |
| WO | 01/84107 A2 | 11/2001 |
| WO | 02/069796 A2 | 9/2002 |
| WO | 03/032808 A2 | 4/2003 |
| WO | 03/086173 A2 | 10/2003 |
| WO | 2004/010844 A2 | 2/2004 |
| WO | 2005/025399 A2 | 3/2005 |
| WO | 2005/103634 A2 | 11/2005 |
| WO | 2005/112745 A1 | 12/2005 |
| WO | 2006/059226 A1 | 6/2006 |
| WO | 2006/097910 A1 | 9/2006 |
| WO | 2006/116569 A2 | 11/2006 |
| WO | 2006/124455 A1 | 11/2006 |
| WO | 2006/130847 A2 | 12/2006 |
| WO | 2007/030331 A1 | 3/2007 |
| WO | 2007/048039 A3 | 4/2007 |
| WO | 2007/056225 A2 | 5/2007 |
| WO | 2007/079316 A2 | 7/2007 |
| WO | 2007/079347 A2 | 7/2007 |
| WO | 2007/101190 A2 | 9/2007 |
| WO | 2007/140422 A2 | 12/2007 |
| WO | 2008/118216 A1 | 10/2008 |
| WO | 2008/157134 A2 | 12/2008 |
| WO | 2009/048659 A1 | 4/2009 |
| WO | 2009/085822 A1 | 7/2009 |
| WO | 2009/100423 A1 | 8/2009 |
| WO | 2009/111542 A2 | 9/2009 |
| WO | 2009/126885 A1 | 10/2009 |
| WO | 2010/004554 A1 | 1/2010 |
| WO | 2010/053617 A2 | 5/2010 |
| WO | 2010053617 A2 | 5/2010 |
| WO | 2010/093865 A1 | 8/2010 |
| WO | 2011/006159 A1 | 1/2011 |
| WO | 2011/053413 A1 | 5/2011 |
| WO | 2011/057084 A2 | 5/2011 |
| WO | 2011/066429 A1 | 6/2011 |

OTHER PUBLICATIONS

Anthony, A., et al., "Effects of Altitude Acclimatization on Rat Myoglobin; Changes in Myoglobin Content of Skeletal and Cardiac Muscle," American Journal of Physiology 196(3):512-516, Mar. 1959.

Antonini, E., and M. Brunori, "The Derivatives of Ferrous Hemoglobin and Myoglobin," in A. Neuberger and E.L. Tatum (eds.), "Hemoglobin and Myoglobin in Their Reactions With Ligands," North-Holland Publishing Co., Amsterdam, 1971, pp. 19-20.

Arakaki, L.S.L., "An Optical Method for Myoglobin Oxygenation Measurements in the Blood-Perfused Rat Hind Limb," doctoral dissertation, University of Washington, Seattle, 1995, 172 pages.

Arakaki, L.S.L., and D.H. Burns, "Multispectral Analysis for Quantitative Measurements of Myoglobin Oxygen Fractional Saturation in the Presence of Hemoglobin Interference," Applied Spectroscopy 46(12):1919-1928, Dec. 1992.

Beebe, K.R., and B.R. Kowalski, "An Introduction to Multivariate Calibration and Analysis," Analytical Chemistry 59(17):1007A-1017A, Sep. 1987.

Caspary, L., et al., "Multicomponent Analysis of Reflection Spectra From the Guinea Pig Heart for Measuring Tissue Oxygenation by Quantitative Determination of Oxygen Saturation of Myoglobin and of the Redox State of Cytochrome $aa_3$, c, and b," Oxygen Transport to Tissue VII: Advances in Experimental Medicine and Biology 191:263-270, 1985.

Cheong, W.-F., et al., "A Review of the Optical Properties of Biological Tissues," IEEE Journal of Quantum Electronics 26(12):2166-2185, Dec. 1990.

Cleman, M., et al., "Prevention of Ischemia During Percutaneous Transluminal Coronary Angioplasty by Transcatheter Infusion of Oxygenated Fluosol DA 20%," Circulation 74(3):555-562, Sep. 1986.

Cope, M., et al., "Data Analysis Methods for Near-Infrared Spectroscopy of Tissue: Problems in Determining the Relative Cytochrome $aa_3$ Concentration," Proceedings of SPIE: Time-Resolved Spectroscopy and Imaging of Tissues 1431:251-262, May 1991.

Cui, W., et al., "Experimental Study of Migration Depth for the Photons Measured at Sample Surface," SPIE Proceedings 1431:180-191, May 1991.

Drabkin, D.L., et al., "The Distribution of the Chromoproteins, Hemoglobin Myoglobin, and Cytochrome c, in the Tissues of Different Species, and the Relationship of the Total Content of Each Chromoprotein to Body Mass," Journal of Biological Chemistry 182(1):317-334, Jan. 1950.

Elwell, C.E., et al., "Quantification of Adult Cerebral Hemodynamics by Near-Infrared Spectroscopy," Journal of Applied Physiology 77(6):2753-2760, Dec. 1994.

Feigl, E.O., "Coronary Physiology," Physiological Reviews 63(1):1-205, Jan. 1983.

Flock, S.T., et al., "Monte Carlo Modeling of Light Propagation in Highly Scattering Tissues: I. Model Predictions and Comparison With Diffusion Theory," IEEE Transactions on Biomedical Engineering 36(12):1162-1168, Dec. 1989.

Gayeski, T.E.J., et al., "Oxygen Transport in Rest-Work Transition Illustrates New Functions for Myoglobin," American Journal of Physiology 248(6 Pt 2):H914-H921, Jun. 1985.

Gayeski, T.E.J., and C.R. Honig, "Intracellular $PO_2$ in Individual Cardiac Myocytes in Dogs, Cats, Rabbits, Ferrets, and Rats," American Journal of Physiology 260(2 Pt 2):H522-H531, Feb. 1991.

Greeley, W.J., et al., "Recovery of Cerebral Metabolism and Mitochondrial Oxidation State Is Delayed After Hypothermic Circulatory Arrest," Circulation 84(5 Suppl):III400-III406, Nov. 1991.

Haaland, D.M., and E.V. Thomas, "Partial Least-Squares Methods for Spectral Analyses. 1. Relation to Other Quantitative Calibration Methods and the Extraction of Qualitative Information," Analytical Chemistry 60(11):1193-1202, Jun. 1988.

Harms, S.J., and R.C. Hickson, "Skeletal Muscle Mitochondria and Myoglobin, Endurance, and Intensity of Training," Journal of Applied Physiology: Respiratory, Environmental and Exercise Physiology 54(3):798-802, Mar. 1983.

Hoffmann, J., and D.W. Lübbers, "Estimation of Concentration Ratios and the Redox States of the Cytochromes From Noisy Reflection Spectra Using Multicomponent Analysis Methods," Oxygen Transport to Tissue VIII: Advances in Experimental Medicine and Biology 200:119-124, 1986.

Hoffmann, J., and D.W. Lübbers, "Improved Quantitative Analysis of Reflection Spectra Obtained From the Surface of the Isolated Perfused Guinea Pig Heart," Oxygen Transport to Tissue VIII: Advances in Experimental Medicine and Biology 200:125-130, 1986.

(56) References Cited

OTHER PUBLICATIONS

Hoffmann, J., et al., "Analysis of Tissue Reflection Spectra Obtained From Brain or Heart, Using the Two Flux Theory for Non-Constant Light Scattering," Oxygen Transport to Tissue VI: Advances in Experimental Medicine and Biology 180:555-563, 1984.

Hoffmann, J., et al., "Simulation of the Optical Properties of an Absorbing and Scattering Medium Using the Monte-Carlo Technique Compared With Two- and Six-Flux Theories," Oxygen Transport to Tissue VII: Advances in Experimental Medicine and Biology 191:883-888,1985.

Holler, F., et al., "Direct Use of Second Derivatives in Curve-Fitting Procedures," Applied Spectroscopy 43(5):877-882, Jul. 1989.

Kagen, L.J., "Chemical Factors," in L.J. Kagen (ed.), "Myoglobin: Biochemical, Physiological and Clinical Aspects," Columbia University Press, New York-London, 1973, pp. 9-13.

Lorber, A., et al., "A Theoretical Foundation for the PLS Algorithm," Journal of Chemometrics 1(1):19-31, Jan. 1987.

Marble, D.R., et al., "Diffusion-Based Model of Pulse Oximetry: In Vitro and In Vivo Comparisons," Applied Optics 33(7):1279-1285, Mar. 1994.

Mark, H.L., and D. Tunnell, "Qualitative Near-Infrared Reflectance Analysis Using Mahalanobis Distances," Analytical Chemistry 57(7):1449-1456, Jun. 1985.

Martens, H., et al., "Improved Selectivity in Spectroscopy by Multivariate Calibration," Journal of Chemometrics 1(4):201-219, Oct. 1987.

Meng, H., et al., "Myoglobin Content of Hamster Skeletal Muscles," Journal of Applied Physiology 74(5):2194-2197, May 1993.

Mohrman, D.E., and E.O. Feigl, "Competition Between Sympathetic Vasoconstriction and Metabolic Vasodilation in the Canine Coronary Circulation," Circulation Research 42(1):79-86, Jan. 1978.

Oshino R. et al., "A Sensitive Bacterial Luminescence Probe for $O_2$ in Biochemical Systems," Biochimica et Biophysica Acta 273(1):5-17, Jun. 1972.

Parsons, W.J., et al., "Dynamic Mechanisms of Cardiac Oxygenation During Brief Ischemia and Reperfusion," American Journal of Physiology 259(5 Pt 2):H1477-H1485, Nov. 1990.

Parsons, W.J., et al., "Myocardial Oxygenation in Dogs During Partial and Complete Coronary Artery Occlusion," Circulation Research 73(3):458-464, Sep. 1993.

Ross, P.D., and P.K. Warme, "Myoglobin as an Oxygen Indicator for Measuring the Oxygen Binding Characteristics of a Modified Myoglobin Derivative Containing Covalently Bound Mesoheme," Biochemistry 16(11):2560-2565, May 1977.

Schenkman, K.A., and D.H. Burns, "Measurement of Myoglobin Oxygen Saturation in the Presence of Hemoglobin Interference by Near-Infrared Spectroscopy," Proceedings of the SPIE 2131:468-474, Jul. 1994.

Schenkman, K.A., et al., "Myoglobin Oxygen Dissociation by Multiwavelength Spectroscopy," Journal of Applied Physiology 82(1):86-92, Jan. 1997.

Severinghaus, J.W., "History and Recent Developments in Pulse Oximetry," Scandinavian Journal of Clinical and Laboratory Investigation 214(Suppl, 214):105-111, 1993.

Shah, N.K., and P.J. Gemperline, "A Program for Calculating Mahalanobis Distances Using Principal Component Analysis," Trends in Analytical Chemistry 8(10):357-361, Nov.-Dec. 1989.

Skov, L., et al., "Estimation of Cerebral Venous Saturation in Newborn Infants by Near Infrared Spectroscopy," Pediatric Research 33(1):52-55, Jan. 1993.

Tamura, M., et al., "Heme-Modification Studies of Myoglobin. II. Ligand Binding Characteristics of Ferric and Ferrous Myoglobins Containing Unnatural Hemes," Biochimica et Biophysica Acta 317(1):34-49, Jul. 1973.

Tamura, M., et al., "In Vivo Study of Tissue Oxygen Metabolism Using Optical and Nuclear Magnetic Resonance Spectroscopies," Annual Review of Physiology 51:813-834, 1989.

Tamura, M., et al., "Optical Measurements of Intracellular Oxygen Concentration of Rat Heart In Vitro," Archives of Biochemistry and Biophysics 191(1):8-22, Nov. 1978.

Thorniley, M.S., et al., "Non-Invasive Measurement of Cardiac Oxygenation and Haemodynamics During Transient Episodes of Coronary Artery Occlusion and Reperfusion in the Pig," Clinical Science (London) 91(1):51-58, Jul. 1996.

Vanderkooi, J.M., et al., "Oxygen in Mammalian Tissue: Methods of Measurement and Affinities of Various Reactions," American Journal of Physiology 260(6 Pt 1):C1131-C1150, Jun. 1991.

Whitfield, R.G., et al., "Near-Infrared Spectrum Qualification via Mahalanobis Distance Determination," Applied Spectroscopy 41(7):1204-1213, Oct. 1987.

Wittenberg, B.A., and J.B. Wittenberg, "Transport of Oxygen in Muscle," Annual Review of Physiology 51:857-878, 1989.

Arai, A.E., et al., "Myocardial Oxygenation In Vivo: Optical Spectroscopy of Cytoplasmic Myoglobin and Mitochondrial Cytochromes," American Journal of Physiology 277(2 Pt 2):H683-H697, Aug. 1999.

Dupuis, L., et al., "Up-Regulation of Mitochondrial Uncoupling Protein 3 Reveals an Early Muscular Metabolic Defect in Amyotrophic Lateral Sclerosis," FASEB Journal 17(4):2091-2093, Nov. 2003.

Extended Search Report dated Nov. 21, 2014, issued in corresponding European National Phase Application No. EP11838800.8, filed Nov. 3, 2011, 9 pages.

International Search Report and Written Opinion dated May 29, 2012, issued in corresponding International Application No. PCT/US2011/059121, filed Nov. 3, 2011, 6 pages.

Laiho, L.H., et al., "Two-Photon 3-D Mapping of Tissue Endogenous Fluorescence Species Based on Fluorescence Excitation and Emission Spectra," Microscopy and Microanalysis 8(S02):1064-1065, Aug. 2002.

Marcinek, D.J., et al., "Mitochondrial Coupling In Vivo in Mouse Skeletal Muscle," American Journal of Physiology-Cell Physiology 286(2):C457-C463, Feb. 2004.

Marcinek, D.J., et al., "Oxygen Regulation and Limitation to Cellular Respiration in Mouse Skeletal Muscle In Vivo," American Journal of Physiology-Heart and Circulatory Physiology 285(5):H1900-H1908, Nov. 2003.

Matcher, S.J., and C.E. Cooper, "Absolute Quantification of Deoxyhaemoglobin Concentration in Tissue Near Infrared Spectroscopy," Physics in Medicine and Biology 39(8):1295-1312, Aug. 1994.

Schenkman, K.A., et al., "Near-Infrared Spectroscopic Measurement of Myoglobin Oxygen Saturation in the Presence of Hemoglobin Using Partial Least-Squares Analysis," Applied Spectroscopy 53(3):325-331, Mar. 1999.

Schrauwen, P., and M.K. Hesselink, "Oxidative Capacity, Lipotoxicity, and Mitochondrial Damage in Type 2 Diabetes," Diabetes 53(6):1412-1417, Jun. 2004.

Search Report and Office Action dated Sep. 2, 2014, issued in corresponding Chinese National Phase Application No. CN 201180062764.8, filed Nov. 3, 2011, 18 pages.

Silverman, A.M., et al., "Shock: A Common Pathway for Life-Threatening Pediatric Illnesses and Injuries," Pediatric Emergency Medicine Practice 2(10):1-22, Oct. 2005.

Wallace, D.C., "A Mitochondrial Paradigm of Metabolic and Degenerative Diseases, Aging, and Cancer: A Dawn for Evolutionary Medicine," Annual Review of Genetics 39:359-407, Dec. 2005.

Yang, Y., et al., "Quantitative Measurement of Muscle Oxygen Saturation Without Influence From Skin and Fat Using Continuous-Wave Near Infrared Spectroscopy," Optics Express 15(21):13715-13730, Oct. 2007.

DETERMINATION OF TISSUE OXYGENATION IN VIVO

CROSS-REFERENCES TO RELATED

This application is a continuation of application Ser. No. 13/883,279, filed May 2, 2013, which is the National Stage of International Application No. PCT/US2011/059121, filed Nov. 3, 2011, which claims the benefit of Provisional Application No. 61/409,793, filed Nov. 3, 2010, the entire disclosures of which are hereby incorporated by reference herein.

BACKGROUND

The benefits of non-invasive systems for detecting and/or monitoring for the presence of a particular analyte are well known in the art, and in particular in the biological arts. For example, in pulse oximetry a sensor is placed on a patient's body, e.g., the patient's finger. The sensor emits a red light and an infrared (IR) light sequentially through the patient, and detects the resulting light transmitted through the patient. The changing absorbance of each of the two wavelengths as the heart beats is measured and used to determine the oxygenation of the pulsing arterial blood alone. The absorbance of the red and IR light is used to calculate the oxygenation of the blood.

Methods and systems for determining and/or monitoring in vivo the oxygenation of tissue in a person or other mammal have a number of applications. For example:

During surgical procedures when a patient is under general anesthesia, it is valuable for clinicians to monitor the patient's perfusion and oxygenation. Low muscle oxygenation will provide an early warning of perfusion and oxygenation problems. An oxygenation monitor would be particularly useful during bypass surgery when pulsatile flow to the body may be limited and pulse oximetry is not a viable option.

Circulatory shock is a life-threatening medical condition that may result in inadequate oxygen to the organs and tissues of the body. Shock includes, for example, traumatic shock, cardiogenic shock, septic shock, neurogenic shock, anaphylactic shock, and the like. In a particular example, a muscle oxygenation probe would be useful in to improve triage and initial medical management, for example in battlefield situations, multi-victim accident situations, and other scenarios involving multiple casualties.

An oxygenation monitor or probe would also be beneficial for refining oxygen titration, including monitoring of neonatal (and premature infant) patients. Muscle oxygen measurement is more sensitive than other existing methods for titration of supplemental oxygen. Better modulation of oxygen support in premature infants and other patients will decrease risks of inadequate oxygen (which can result in brain or other organ damage) as well as excessive oxygen therapy (which can result in long-term lung injury).

A tissue oxygenation monitor would be beneficial in exercise physiology and sports medicine applications. In particular, muscle oxygenation is an indicator of aerobic capacity, muscle anaerobic metabolism, and performance.

Measuring muscle oxygenation during transport of patients and during pre-hospital admission as part of early evaluation could lead to earlier treatment and better outcome.

Often trauma can lead to blood vessel compression by the raised pressure within a body compartment, and ultimately to lack of oxygenation and tissue death. A tissue oxygenation probe would help identify decreasing oxygenation and increasing tissue death so treatment can be initiated early.

An in vivo oxygenation probe may be used to determine viability of tissue to be transplanted and to monitor the progress of reperfusion in the transplanted organ.

An in vivo oxygenation probe may be used to detect and/or monitor for peripheral vascular disease and/or during arterial and vascular surgery to aid in the identification of tissue perfusion status. The probe would be especially helpful in identification of tissue viability in extremities with vascular disease, for example, helping the surgeon to determine whether and where to perform amputations.

Muscle oxygenation or saturation can be used as an early or leading signal of circulatory shock. Shock is a life-threatening medical condition characterized by "inadequate substrate for aerobic cellular respiration." Silverman, Adam (October 2005). "Shock: A Common Pathway for Life-Threatening Pediatric Illnesses and Injuries," *Pediatric Emergency Medicine Practices* 2(10). In its early stages, shock may be described generally as inadequate oxygen levels in tissue. Several conditions can trigger the onset of shock, including, for example, sepsis, heart dysfunction, and hemorrhage. If left untreated, shock can lead to Multiple Organ Dysfunction Syndrome (MODS) and even death.

A clinically important aspect of circulatory shock is that it progresses by one or more positive feedback mechanisms, and therefore can rapidly escalate to permanent damage or death if left untreated. Early detection of shock is critical to optimize patient outcomes as well as to reduce the costs for medical treatment.

Current methods of recognizing shock are indirect, non-definitive, or slow. These methods include monitoring vital signs, which are non-specific, and sampling blood chemistry, which has associated metabolic and procedural delays. High lactate levels indicate a metabolic response to the presence of shock, but they lag decreases in muscle and systemic oxygenation that occur at the onset of shock. Invasive catheters are not used to detect shock, but may be used in cases of known severe shock. These catheters are expensive and must be inserted by highly trained personnel.

Continuous measurement of muscle oxygenation would also allow physicians to refine therapy as normalization of cellular oxygenation is achieved, giving patients what they need while preventing over-resuscitation. It is well established that unnecessary blood transfusions and excess fluid administration worsen outcome.

At this time, there are several commercial near infrared spectroscopy (NIRS) devices that are being used in various areas of health and physiology. Traditional NIRS devices measure 2 to 6 discrete wavelengths in the near infrared region. Exemplary NIRS devices are disclosed in U.S. Patent Application Publication No. 2011/0205535, to Soller et al., the disclosure of which is hereby incorporated by reference in its entirety.

There remains a need for improved methods, systems, and devices for detecting and monitoring the oxygenation of tissue. There is also a clinical need for improved methods, systems, and devices for monitoring patients to rapidly detect circulatory shock.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

As discussed above, the detection of tissue oxygenation in vivo would have a number of uses. Methods and apparatus for detecting tissue oxygenation are disclosed herein.

A system for determining muscle oxygenation in a body includes a probe comprising a housing having a housing face configured to abut the body; a processor connected to control a first light source operable to emit light at a first radiant flux in a visible wavelength range from one or more first emission locations on the housing face, and further connected to control a second light source operable to emit light at a second radiant flux in a near-infrared wavelength range from one or more second emission locations on the housing face such that the visible light emitted by the first light source and the near-infrared light emitted by the second light source are directed into the abutting body, wherein the first radiant flux is greater than the second radiant flux; and a light detector system configured to receive light from the body at a receiving location on the housing face and to transmit spectral information characterizing the received light to the processor. The processor is configured to calculate a muscle oxygenation based on the spectral information transmitted by the light detector system.

In an embodiment the receiving location is uniformly spaced from all of the one or more first emission locations and the one or more second emission locations.

In an embodiment the one or more first emission locations comprises a plurality of first emission locations, and further wherein the plurality of first emission locations and the one or more second emission locations are disposed along a circular arc centered on the receiving location.

In an embodiment the light detector system comprises a spectrometer, and further comprising an optical cable that transmits light from the receiving location on the abutting housing face to the spectrometer.

In an embodiment the light detector system comprises a spectrophotometer operably configured to receive light from the receiving location on the housing face.

In an embodiment the visible wavelength range is within the range of 540-620 nm.

In an embodiment the near-infrared wavelength range is within the range of 740-790 nm.

In an embodiment the first radiant flux is produced by a plurality of light emitting diodes.

In an embodiment the one or more first emission locations on the abutting face of the housing comprise a plurality of locations disposed along a circular arc defining about one quarter of a circle centered on the receiving location.

In an embodiment the first radiant flux is at least an order of magnitude greater than the second radiant flux.

In an embodiment the first light source and the second light source are controlled to synchronously emit light simultaneously.

In an embodiment the processor is configured to use the transmitted spectral information to calculate (i) a first sum of a concentration of oxymyoglobin and a concentration of oxyhemoglobin, (ii) a second sum of a concentration of deoxymyoglobin and a concentration of deoxyhemoglobin, and (iii) a muscle oxygenation based on the first sum and the second sum.

A system for detecting circulatory shock includes a probe comprising a housing having a housing face configured to abut a body; a processor connected to control a first light source operable to emit light at a first radiant flux in a visible wavelength range from one or more first emission locations on the housing face, and further connected to control a second light source operable to emit light at a second radiant flux in a near-infrared wavelength range from one or more second emission locations on the housing face such that the visible light emitted by the first light source and the near-infrared light emitted by the second light source are directed into the abutting body, wherein the first radiant flux is greater than the second radiant flux; and a light detector system configured to receive light from the body at a receiving location on the housing face and to transmit spectral information characterizing the received light to the processor. The processor is configured to calculate a muscle oxygenation based on the spectral information transmitted by the light detector system, and to activate an alert if the calculated muscle oxygenation is below a predetermined threshold, thereby indicating a potential clinical concern for circulatory shock.

In one embodiment, tissue oxygenation may be defined as myoglobin saturation, where myoglobin saturation is calculated from [oxyMb] and [deoxyMb], and oxyMb is oxymyoglobin and deoxyMb is deoxymyoglobin. The concentrations [oxyMb] and [deoxyMb] are calculated from each detected absorbance spectrum.

In another embodiment, tissue oxygenation may be defined as hemoglobin saturation, where hemoglobin saturation is calculated from [oxyHb] and [deoxyHb], and oxyHb is oxyhemoglobin and deoxyHb is deoxyhemoglobin. The concentrations [oxyHb] and [deoxyHb] are calculated from each detected absorbance spectrum. Hemoglobin saturation includes contributions from pulsatile arterial blood, non-pulsatile arterial blood, and venous blood.

The same method for determining tissue oxygenation in vivo as described above, consisting of generating an in vivo training set, obtaining similar spectral data from a patient using a similar probe, and using the spectral data from the patient and the training data to calculate tissue oxygenation from the patient may be used.

A probe for detecting in vivo tissue oxygenation in a subject includes (a) a first light source operable to emit light in a visible spectrum having a first radiant flux, (b) a second light source operable to emit light in a near-infrared spectrum having a second radiant flux that is greater than the first radiant flux, and (c) a light detector operable to detect absorbance spectra of light reflected from or transmitted through a tissue of the subject resulting from light emitted by the first and second light sources.

In an embodiment, the first radiant flux is at least an order of magnitude greater than the second radiant flux and comprises a plurality of lighting elements that cooperatively produce the second radiant flux. The plurality of lighting elements are preferably disposed along a circular arc centered on the light detector, which in a particular embodiment extends for not more than 90°.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Non-invasive methods, apparatuses, and systems for detecting an analyte in a turbid medium such as a biological tissue are disclosed. There are many biological and medical applications wherein a non-invasive means for determining oxygenation in a tissue would provide benefits. For example, tissue oxygenation provides an early signal of potential problems in physiology and pathology. A system for monitoring muscle oxygenation could also be applied in clinical areas such as cardiac surgery, in sports medicine, and the like. In a particular embodiment, a device and method for monitoring muscle oxygenation (Mox) to provide early detection of shock in a patient is described. It will be readily appreciated by persons of skill in the art that the teachings of the present invention may be readily applied to other applications, including the exemplary applications discussed in the Background section above.

In U.S. Pat. No. 5,931,779, to Arakaki et al., which is hereby incorporated by reference in its entirety, some of the present inventors disclosed a method and system for real-time in vivo measurement of myoglobin oxygen saturation. In U.S. Patent Application Publication No. 2007/0265513, to Schenkman et al., which is hereby incorporated by reference in its entirety, some of the present inventors disclosed a system and method for determining a mitochondrial characteristic using calibration spectra and a reflectance spectrum. In U.S. Patent Application Publication No. 2008/0033263, to Marcinek et al., which is hereby incorporated by reference in its entirety, some of the present inventors disclosed a system and method for calculating a ratio of hemoglobin and myoglobin based on peak positions between spectral peaks. In U.S. Patent Application Publication No. 2008/0200780, to Schenkman et al., which is hereby incorporated by reference in its entirety, some of the present inventors disclosed a system and method for generating an estimate of a cellular energetic parameter using a multivariate curve resolution algorithm.

In contrast to prior art near infrared spectroscopy systems, a system 100 in accordance with the present invention measures continuous wavelengths of light in both the visible spectrum and the near infrared (NIR) spectrum. The addition of at least a portion of the visible region of the spectrum allows enhanced sensitivity to muscle oxygenation and more rapid detection of circulatory shock. Visible light, as used herein, is expressly defined to comprise electromagnetic radiation having a wavelength in the range of 400-700 nm. Near infrared light, as used herein, is expressly defined to comprise electromagnetic radiation with a wavelength in the range of 700-3,000 nm.

Figure 1:
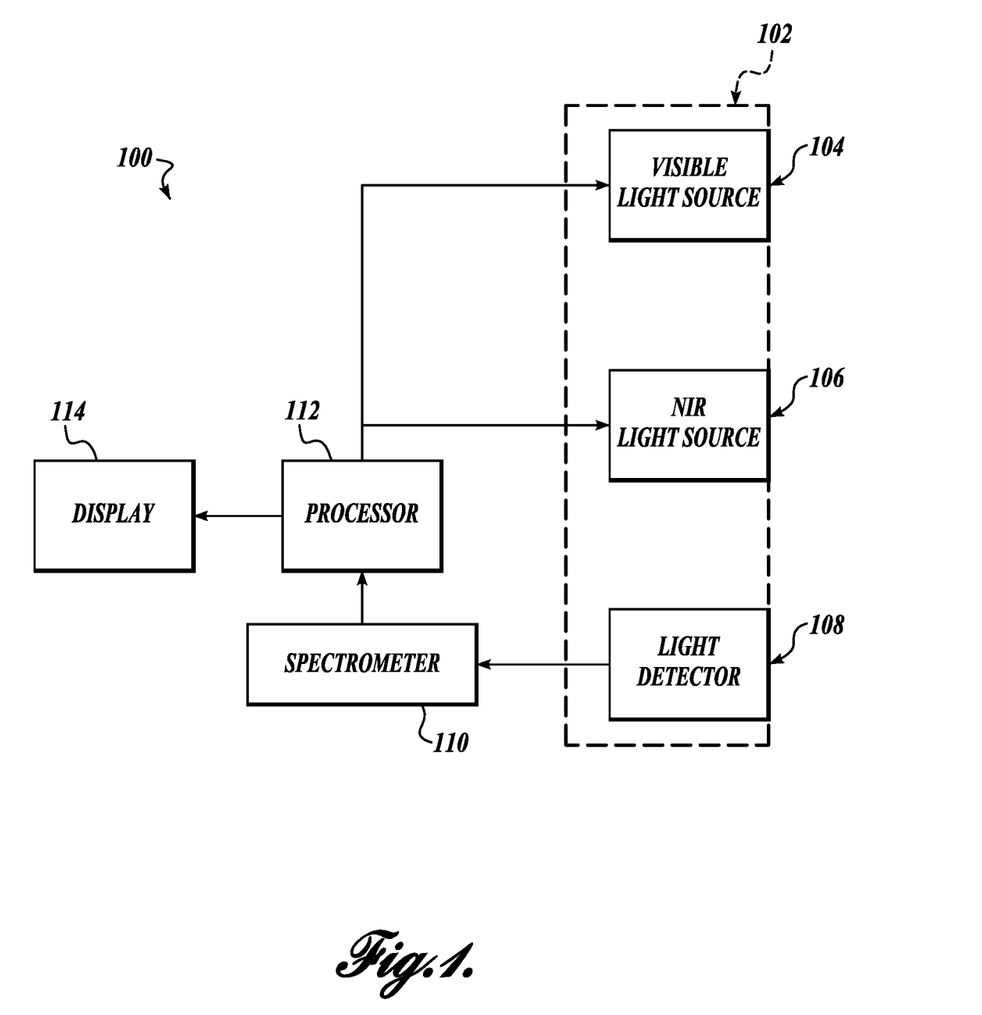
FIG. 1 is a block diagram providing an overview of a system for measuring and/or monitoring the oxygenation of tissue in vivo in accordance with the present invention.

FIG. 1 is a block diagram providing an overview of a system 100 for measuring and/or monitoring the oxygenation of tissue in vivo in accordance with the present invention. The system 100 includes a probe 102 having a visible light source 104, an NIR light source 106, and a light detector 108. The visible light source 104 and NIR light source 106 illuminate a desired region of tissue adjacent the probe 102. For example, the visible and NIR light may transmit through a user's skin and fluids to illuminate the desired region of tissue.

The light detector 108 receives light reflected from or transmitted through the desired region of tissue, and transmits the detected light to a spectrometer, spectrophotometer, or the like 110. Various types of spectrometers 110 are contemplated, including those having a sensor and a prism, diffraction grating, or slit. Both the prism (or grating or slit) and the sensor may be stationary or swept. For example, an exemplary system 100 includes a fiber-optic spectrophotometer 110 having a grating and a photodetector, such as a photodiode array, a charge-coupled device (CCD), or a complementary metal-oxide-semiconductor device such as an active pixel sensor (CMOS APS).

The detected spectra are transmitted to a processor, for example, a conventional computer system 112 for processing. The particular details of the computer system 112 are not critical to the present invention. In an exemplary system, the computer system 112 includes an input interface for coupling to an analog-to-digital converter to receive spectral data. Well-known components may comprise the computer system 112, such as a keyboard, mouse, trackball, touchpad, printer, an interface, and other elements configured for controlling or monitoring components of system 100.

The computer system 112 may further control the visible and NIR light sources 104, 106. In a current embodiment, for example, the visible light source 104 and the NIR light source 106 are controlled to synchronously emit light intermittently. The computer system 112 includes a processor configured to execute instructions for implementing an algorithm described elsewhere in this document. The instructions, algorithm, and data can be stored in memory or received from an input. The memory, in various examples, includes a volatile or non-volatile memory or storage device. Typically, a display device 114 may be used to display the status of the system 100 and/or the results of the analysis of the spectra. For example, the display device 114 may include a visual or audible alert to notify a healthcare provider if the results of the analysis indicate the need for remedial action.

In an embodiment of the present invention adapted to monitor for shock, the probe 102 is attachable to the patient, for example, over the thenar muscle group in the hand. The visible and NIR light sources 104, 106 illuminate muscle tissue, and the reflected light returning to the spectrometer 110 is recorded. The spectra are provided to the computer system 112 for analysis, as described below, to calculate muscle oxygenation (Mox). If the Mox indicates that the patient is experiencing circulatory shock, the caregiver is alerted to take appropriate action.

Mox was found to be an early indicator of shock. Moreover, Mox can be used to differentiate between mild, moderate, and severe shock. Low Mox in critically ill patients can be used to identify the early stages of shock since blood flow is preferentially shunted away from skin and muscle as the body tries to preserve blood flow to the critical organs of the body—the heart, brain, and liver.

Mox is a measure of cellular oxygenation in muscle tissue and is a weighted average of myoglobin and hemoglobin oxygen saturations. The weighting depends on the relative concentrations of total myoglobin and total hemoglobin in the light path.

In another embodiment, the computer system 112 can perform analyses to calculate tissue oxygenation defined as myoglobin saturation. Since myoglobin is contained within muscle cells, myoglobin saturation is a measure of intracellular oxygenation that will be useful in the detection of shock and the monitoring of critically ill patients.

In another embodiment, tissue oxygenation can be defined as hemoglobin saturation. Hemoglobin saturation measurements would not depend on the patient having pulsatile blood flow; it is an aggregate saturation measurement of pulsatile arterial blood, non-pulsatile arterial blood, and venous blood. Hemoglobin saturation can be measured in muscle tissue and in other tissues that do not contain myoglobin, such as the brain.

In an embodiment of the monitoring system 100, the probe 102 is configured to illuminate the tissue with a sculpted or shaped intensity (or radiant flux) illumination that improves the usefulness of the reflectance or transmission of the optical spectral information obtained. For example, in a current embodiment the visible light source 104 is configured to illuminate the desired tissue with light in a visible region (e.g., 545-580 nm) having a radiant flux that is an order of magnitude larger than the NIR illumination provided by the NIR light source 106. By matching the profile of the incident illumination to the expected absorbance of the tissue, the signal-to-noise ratio of the detected spectra can be optimized, resulting in higher quality optical spectra than can be acquired with a traditional broadband light source. It is contemplated that the visible light source 104 will produce a significantly larger radiant flux than the NIR light source, although the difference may be less than, or greater than, an order of magnitude.

Figure 2:
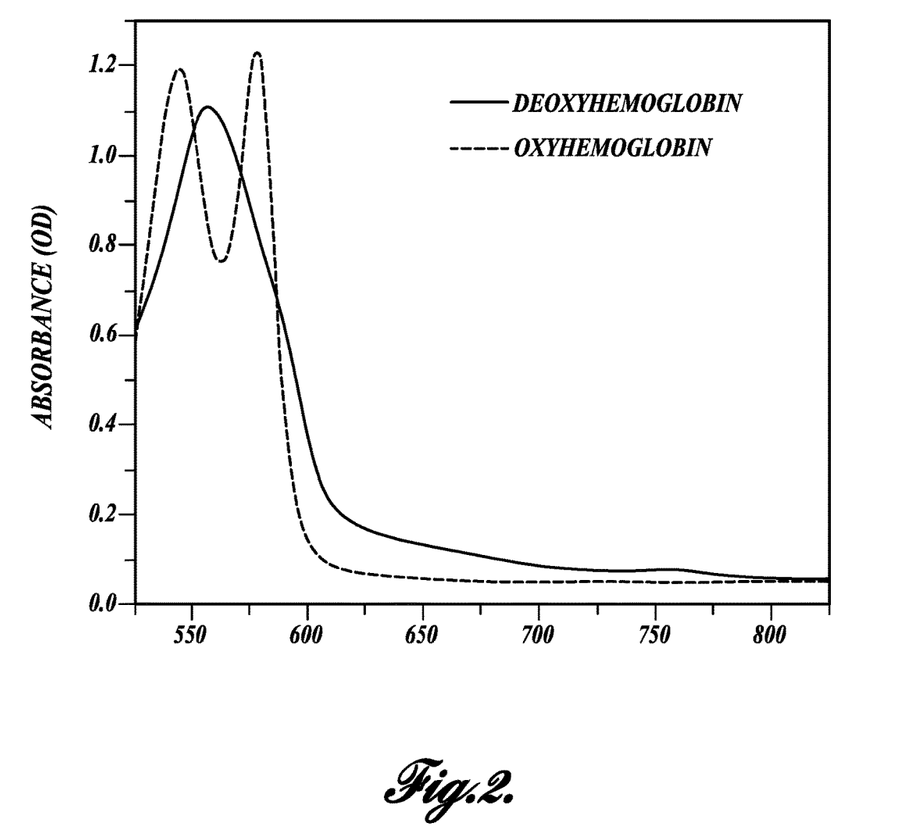
FIG. 2 shows the absorbance spectrum of solutions of oxyhemoglobin and deoxyhemoglobin.

To understand the reason for the improved performance from the sculpted illumination refer to FIG. 2, which shows the absorbance spectrum of solutions of oxyhemoglobin and deoxyhemoglobin. Hemoglobin in the blood binds with oxygen and carries oxygen from the lungs to the body tissues where it releases the oxygen and carries the resultant carbon dioxide back to the lungs. Oxyhemoglobin is formed when hemoglobin binds with oxygen; deoxyhemoglobin is formed when no oxygen molecules are bound to hemoglobin. (Myoglobin is an oxygen-binding protein in muscle tissue and may similarly be bound to oxygen molecules (oxymyoglobin) or not bound to oxygen molecules (deoxymyoglobin)).

It can be seen from FIG. 2 that the absorbance spectrum for oxyhemoglobin differs from the absorbance spectrum for deoxyhemoglobin. The differences in the absorbance characteristics may be used to optically evaluate the oxygenation of the hemoglobin. The ability to accurately evaluate the oxygenation will be improved by looking at features of the oxygenation curve in both the visible light region and the NIR region. However, the peaks of the absorbance or optical density for oxyhemoglobin in the visible region (and more particularly in the range of 545-580 nm) are about an order of magnitude larger than the peak of the absorbance of deoxyhemoglobin in the NIR region (e.g., approximately 760 nm). Therefore, if a conventional broadband light source is used, the amount of light collected in the visible region will be about ten times smaller than that collected in the NIR region. Moreover, FIG. 2 illustrates a best-case scenario because the absorbance spectra were collected from a solution of hemoglobin that did not include a scatterer. When light scattering is significant, as in biologic tissue, the collected light from the visible region can be as much as three orders of magnitude smaller than in the NIR region. The absorbance spectrum for oxymyoglobin and deoxymyoglobin also differ in a qualitatively similar way. The differences in the absorbance spectra can be analyzed to calculate tissue oxygenation (e.g., Mox, myoglobin saturation, or hemoglobin saturation).

However, if a conventional broadband light source (across the visible and NIR regions) is used to acquire spectra from biologic tissue that includes hemoglobin, the detector may be unable to detect a measurable signal in the visible region (e.g., no visible range photons may be detected) or the detector may become saturated in the NIR region (e.g., more NIR photons arrive than the detector can count, so a maximum value is registered). In either case, the dynamic range of the detector may not be large enough to measure both the visible and the NIR region spectra simultaneously.

The probe light sources 104, 106 produce a sculpted illumination having an intensity or radiant flux profile that is generally matched to the expected absorbance spectrum. In other words, the radiant flux of the illumination in wavelength regions with high absorbances is higher than the radiant flux of the illumination in wavelength regions with lower absorbances. In a preferred embodiment, the visible light source 104 is configured to illuminate the target tissue with a radiant flux that is an order of magnitude, or more, greater than the corresponding radiant flux produced by the NIR light source 106.

A number of different methods may be used to approximately match the illuminating light with the absorbance characteristics of the target and are contemplated by the present invention. For example, filters may be used with a broadband light source to produce the desired sculpted illumination. In a currently preferred embodiment, the visible light source 104 and the NIR light source 106 are implemented with light-emitting diodes (LED) disposed to emit light from a distal face of the probe 102. Although the disclosed probe uses LEDs that are disposed at the face of the probe 102, other configurations are contemplated. For example, in a fiber optic embodiment the light sources are disposed away from the probe 102 and light is transmitted to the probe face through fiber optic cables.

Figure 3:
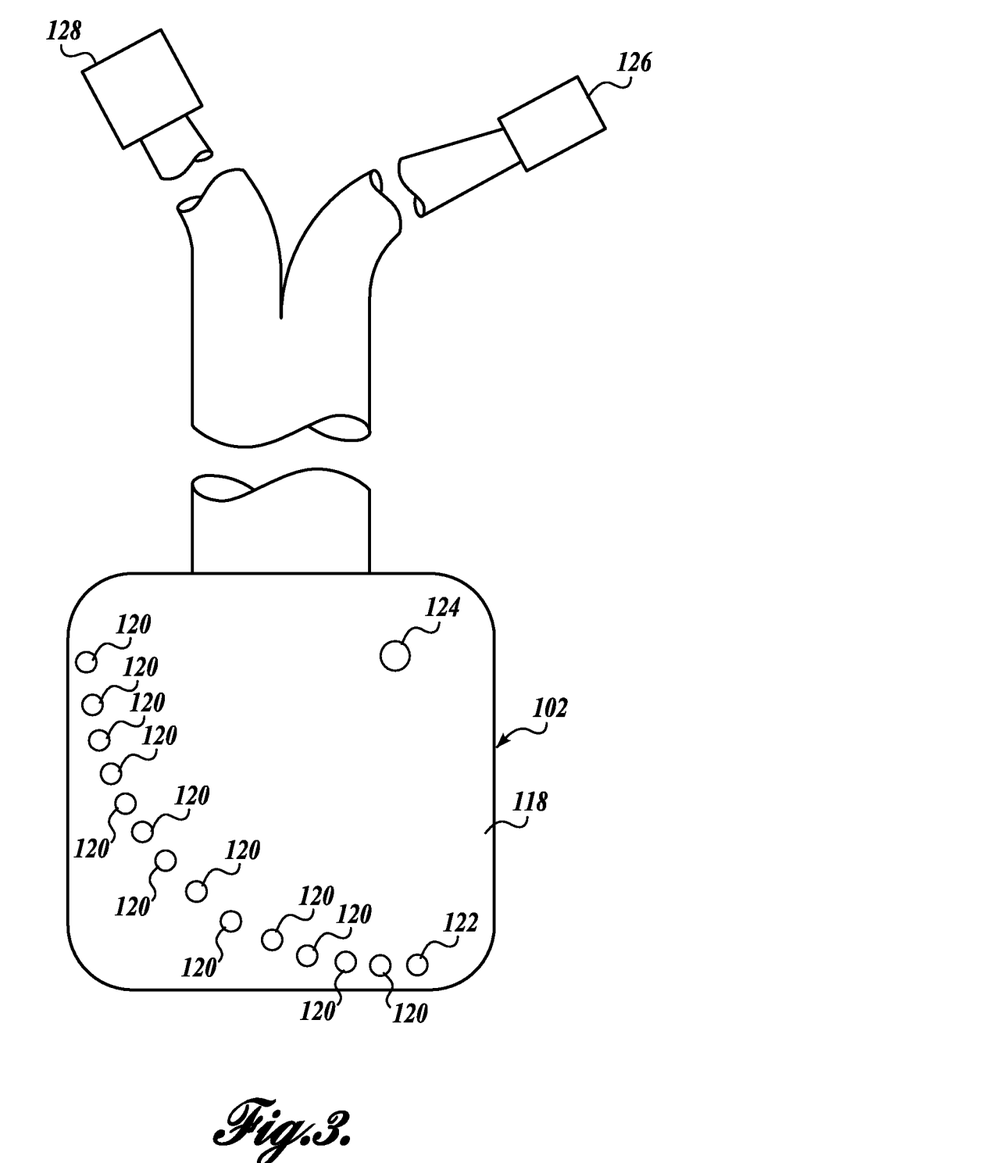
FIG. 3 illustrates an embodiment of the probe shown in FIG. 1.

FIG. 3 illustrates an embodiment of the probe 102 shown in FIG. 1 having a housing 118 that is configured to be placed against the user or tissue to be examined. The housing 118 may be rigidly constructed or may be conformable to the user. The visible light source 104 comprises a plurality of LEDs 120 that emit light in visible wavelengths (e.g., 540-620 nm), and the NIR light source 106 is a single LED 122 that emits in the NIR wavelengths (e.g., 740-790 nm). In this embodiment the probe 102 includes 13 visible light LEDs 120. The probe 102 is configured to illuminate the target tissue such that the intensity of the visible light illumination is approximately an order of magnitude greater than the intensity of the NIR illumination.

A light detector 108, for example a conventional CMOS photodetector 124 is positioned in the housing 118 to detect light reflected from the target tissue. Preferably, the visible light LEDs 120 and the NIR LED 122 are all disposed along a circular arc centered on the detector 124 such that the LEDs 120, 122 are all the same distance from the detector 124. The distance from the LEDs 120, 122 to the detector 124 is selected to optimize light collection, depending on characteristics of the tissue and the spectral information being collected. In particular, the distance between the LEDs and the detector is selected to provide a desired depth of penetration into the tissue. This allows for homogeneous sampling of the tissue in a known tissue volume.

Although it is not critical to the present invention, it should be appreciated that the LEDs 120, 122 in this embodiment are disposed along a circular arc that comprises approximately a 90° arc segment rather than a complete circle centered on the detector 124. This configuration advantageously allows for large spacings between the LEDs and the detector (e.g., 15-20 mm), while keeping probe sizes reasonable. The known and constant spacings between LEDs and detector provide for a constant depth of light penetration into the tissue from the skin surface. The LEDs 120, 122 and/or the detector 124 are preferably disposed in the housing 118 such that the detector 124 is shielded from stray light.

The probe 102 further includes a first connector 126 that engages the computer system 112 to control the visible and NIR LEDs 120, 122, and a second connector 128 that engages to transmit the light signal from the detector 124 to the spectrometer 110.

In another embodiment, the visible and NIR light sources 104, 106 are generated remotely from the face of the probe, and a first fiber optic system is used to transmit the light to the face of the probe, and a second fiber optic system returns the light from the detector 124 to the spectrometer 110.

The probe 102 is configured to collect reflectance spectral information non-invasively. The probe may be used to collect, for example, reflectance optical spectra in humans or other mammals for medical diagnostics, exercise physiology, and the like.

In studies by the present inventors, it was found that Mox is effective for the early detection of shock. In a recent study, spectra were acquired from the thenar muscles of 20 healthy human subjects to build a locally weighted regression (LWR) model that is used to provide real-time measurement of Mox in other subjects. LWR is a nonparametric learning algorithm that modifies a conventional linear or nonlinear least squares regression model by introducing a weighting scheme to give greater effect to "local" data points, and less weight to more distant data points.

The spectral data from the healthy subjects were obtained using the following basic protocol. Each of the subjects was monitored using a system functionally similar to the monitoring system 100 shown in FIG. 1, with the probe 102 disposed over the subject's thenar muscle group. The subject breathed room air and then 100% oxygen, and then underwent a 15-minute period of arm ischemia produced by inflation of a blood pressure cuff on the upper arm while spectral data were collected.

The spectra from each subject were analyzed using Multivariate Curve Resolution (MCR). MCR is a group of spectral techniques known in the art. In the present method, MCR is used to yield accurate measurements of Mox from the spectra obtained from the subjects. However, MCR is not practical for real-time measurements because of its iterative nature. The MCR values for Mox and the spectra were used to train an LWR model and produce the model, as described more fully below.

Figure 4:
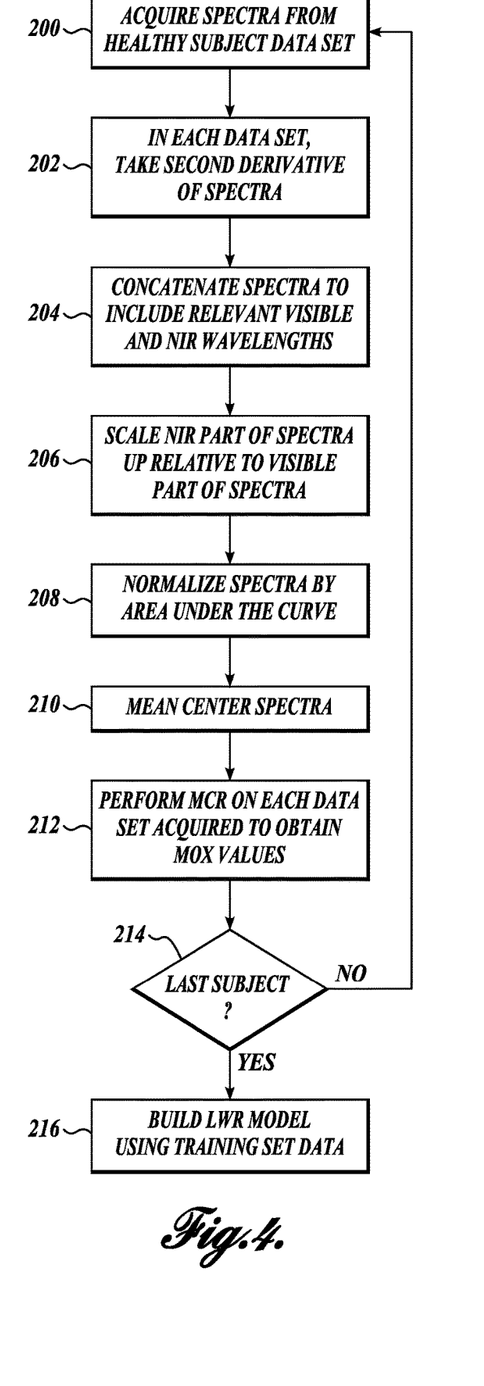
FIG. 4 is a flow chart illustrating a method for generating a useful set of training data in accordance with the present invention.

The currently preferred protocol for obtaining the spectral data from the healthy subjects, and the preferred method for generating a useful set of training data will now be described in more detail, with reference to the flow chart of FIG. 4. First, datasets of spectra from healthy subjects are obtained 200. Each of the healthy subjects undergoes a period of 3 minutes of rest while breathing air followed by 3 minutes of rest while breathing 100% oxygen. Ischemia is then produced in the subject's arm for a 15-minute period by inflation of a blood pressure cuff around the subject's upper arm to 200 mmHg or 60 mmHg above systolic blood pressure, whichever is less. A 5-minute recovery period follows to ensure normal circulation has been established. Spectra are acquired throughout the protocol using a system functionally similar to the system 100 described above.

Second derivatives with respect to wavelength are taken of each spectrum 202. Using the second derivative of the spectra makes the distinctions between oxygenated and deoxygenated spectra greater and removes some of the effects of scattering.

In the current embodiment, only those portions of the collected spectra that correspond to the interesting portions of the spectrum are used in the analysis. As discussed above, the interesting peaks of the absorbance spectrum for oxyhemoglobin, deoxyhemoglobin, oxymyoglobin, and deoxymyoglobin are generally in the visible region around 580 nm (e.g., 570-588 nm) and in the near infrared region around 760 nm (e.g., 740-777 nm). The selected interesting portions of each of the collected spectra are extracted and concatenated to produce spectra for analysis that include only the most relevant portions of the visible and NIR spectra 204. Including only the relevant portions of the spectrum in the analysis filters out noise and makes the analysis more sensitive to Mox.

More generally, in biologic tissues or samples, many optically active species may be present. In order to improve multi-wavelength spectral analysis, aspects of the spectrum information can be amplified over background spectrum information (or noise) by selection of desired spectrum regions. When these selected spectrum regions are concatenated into a new spectrum array, the information can be analyzed by conventional methods of analysis, for example, by MCR, and the result is improved measurement of analyte concentrations of interest.

In the present specific example, the analysis of concatenated portions of the spectrum data around known peaks for oxymyoglobin, deoxymyoglobin, oxyhemoglobin, and deoxyhemoglobin enhances the analysis using a spectral methods approach, such as MCR. Measurement of reflected light in the visible region around 580 nm yields information about concentrations of oxymyoglobin and oxyhemoglobin because these chromophores absorb in this region. Absolute quantification of myoglobin and hemoglobin saturation is made possible by the addition of measurements of concentrations of deoxymyoglobin and deoxyhemoglobin. These chromophores absorb in the NIR region around 760 nm.

Keeping and analyzing only wavelength regions around where the oxygenated and deoxygenated forms of myoglobin and hemoglobin absorb has proven effective. MCR is an iterative algorithm that uses least squares fitting to determine the shape of each chromophore spectrum present in the sample. The inventors believe that MCR is given a better chance of converging on the correct absorbance characteristics of the chromophores by removing or ignoring the less-interesting portions of the spectra, including the noise and absorbance from other chromophores present in tissue. The selection and concatenation of non-contiguous wavelength regions before spectral analysis would benefit the analysis of other types of spectrum data. For example, in another application it is contemplated that spectrum regions around cytochrome oxidase or cytochrome c absorbances may be selected to improve measurement of cytochrome oxidase or cytochrome c concentrations or oxidations.

The NIR portion of each concatenated spectrum is scaled up relative to the visible portion of the spectrum 206. The magnitudes of the NIR absorbances are much smaller than those of the visible absorbances. Although the scaling step is not critical to the present invention, without scaling the normalization may bias MCR toward erroneously oxygenated Mox values.

The concatenated spectra are then scaled (normalized) 208, for example, such that the areas under each of the curves is equal to one. Normalization is needed as a preparatory step for MCR. Mean centering is then applied to all spectra 210.

Mox must be determined from each spectrum in the training set. In the currently preferred method, MCR is used to obtain Mox values for each spectrum in a data set 212. MCR is an iterative spectral analysis method that can determine the individual concentrations of absorbing species within complex spectra. In one embodiment, in each iterative step MCR simultaneously quantifies concentrations of two components in each spectrum, oxyMbHb and deoxyMbHb, where by definition:

[oxyMbHb]=[oxymyoglobin]+[oxyhemoglobin], and

[deoxyMbHb]=[deoxymyoglobin]+[deoxyhemoglobin].

In every iterative step, MCR also uses the current estimates of component concentrations to determine the shape of the pure component spectra. When MCR has converged on the shape of the pure component spectra of oxyMbHb and deoxyMbHb and their relative concentrations in each spectrum in the data set, Mox is calculated from each spectrum in a subject's data set as:

Mox={[oxyMbHb]/([oxyMbHb]+[deoxyMbHb])}*100    (1)

Myoglobin saturation (Mb sat) may also be calculated from MCR determination of [oxyMb] and [deoxyMb]:

Mb sat={[oxyMb]/([oxyMb]+[deoxyMb])}*100

The concentrations of [oxyHb] and [deoxyHb] can also be determined by MCR, resulting in a calculation of hemoglobin saturation (Hb sat):

Hb sat={[oxyHb]/([oxyHb]+[deoxyHb])}*100

The concentrations [oxyMb], [deoxyMb], [oxyHb], and [deoxyHb] may be determined simultaneously using MCR. Hemoglobin saturation may be determined using MCR in tissues where myoglobin is not present.

If additional healthy subjects are to be included 214, the data collection proceeds with the additional subjects. Spectra from a number of subjects and associated Mox, Mb sat, or Hb sat values for each spectrum, determined with MCR, comprise the training set. The set of training data calculated from the test subjects may then be used to build an LWR model 216.

Figure 5:
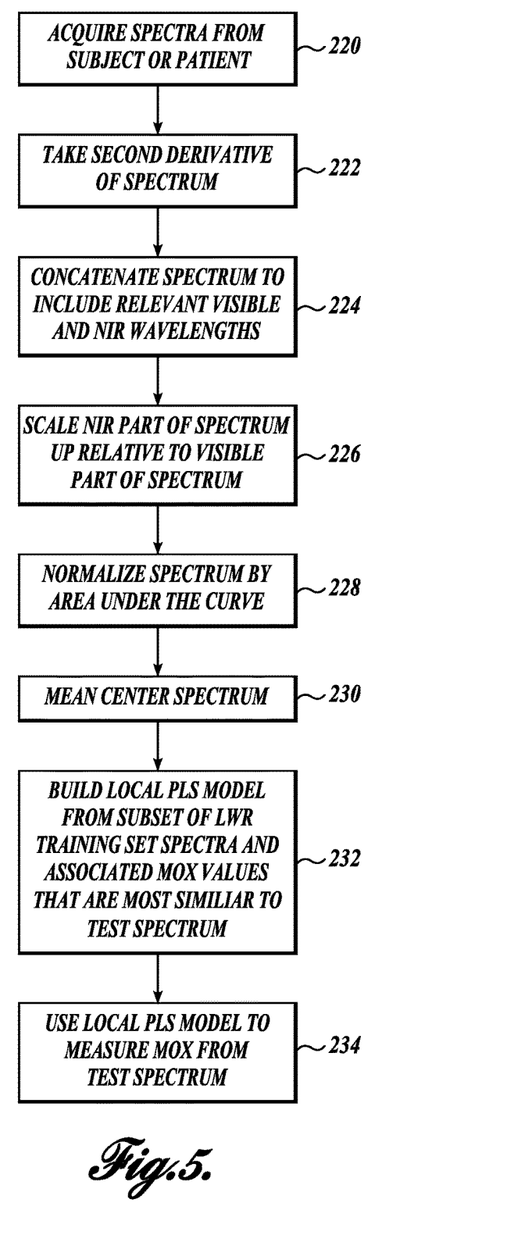
FIG. 5 is a flow chart illustrating a method for using the training data obtained by the method illustrated in FIG. 4.

The LWR model provides for real-time monitoring or testing of patients or other subjects. As illustrated in FIG. 5, when spectra are collected from a patient 220, the spectra are preprocessed in the same way the LWR training set spectra were processed, including taking the second derivative 222, concatenating the selected portions 224, scaling the NIR portion 226, normalization 228, and mean centering 230.

In prior work, the present inventors have used partial least squares (PLS) to effectively measure myoglobin saturation in skeletal and cardiac muscle. Unfortunately, the global PLS method trained with spectra collected in vitro does not allow real-time measurement of Mox. The currently preferred method therefore uses locally weighted regression (LWR) with PLS to calculate Mox from spectra in real time. In particular, for each new spectrum acquired from a patient, LWR builds a local PLS model from spectra in the in vivo training set 232 that are most similar to the new spectrum. The LWR method does not allow, for example, training set spectra with vastly different melanin and lipid characteristics from the new spectrum to contribute to its Mox measurement. This essentially creates an effective filter for spectrum characteristics that reflect melanin and lipid content and that are unrelated to Mox. Mox is calculated from each test set spectrum by application of the local PLS model 234.

When spectra in the LWR training set encompass a wide range of physical characteristics found in patients, the robustness of the Mox measurement is improved by assuring that appropriate training set spectra are available. Good accuracy in human subjects has been demonstrated using LWR with a relatively small training set.

Other types of LWR models can be built to measure tissue oxygenation. Mb sat may be measured from spectra in the training set and used to build an LWR model that will measure Mb sat from patient spectra. Similarly, Hb sat may be measured from training set spectra collected from tissue that either does or does not contain myoglobin. These Hb sat values may be used with the training set spectra to build an LWR model that will measure Hb sat from patient spectra.

EXAMPLES

Muscle oxygenation is an early indicator of shock, and it can differentiate mild, moderate, and severe shock from the healthy state. In a study, Mox was measured as soon as possible after emergency department admission for 15 minutes in each of 57 trauma patients. Shock severity in each patient was determined using a scoring system based on maximum arterial lactate or base deficit, maximum heart rate, and minimum systolic blood pressure recorded during the first hour after the start of spectral acquisition Mox during mild, moderate, and severe shock were significantly different from healthy controls ($p<0.01$).

New Zealand white rabbits were subjected to hemorrhagic shock by withdrawal of blood in three increments. The key result is that Mox can detect the onset of shock. After transitioning the rabbit from 100% $O_2$ to air, Mox significantly decreased from baseline values after the first blood withdrawal. At this same point, lactate was still normal. Mox progressively decreased during moderate and severe shock, and then increased with resuscitation. Mox closely followed trends in mean arterial pressure (MAP) that was measured via a catheter placed in the carotid artery. Lactate levels rose during shock and decreased with resuscitation, but lagged in time behind changes in MAP and Mox. Arterial blood saturation measured by pulse oximetry was not sensitive to shock. This study demonstrates the potential of Mox to detect shock early and to continuously monitor patient condition during resuscitation.

Spectra were acquired continuously in a rabbit subjected to hemorrhagic shock by withdrawal of about 40% of the total blood volume in three equal increments. A four-component Multivariate Curve Resolution (MCR) analysis was used to simultaneously measure concentrations of oxymyoglobin, deoxymyoglobin, oxyhemoglobin, and deoxyhemoglobin. Calculation of Mb saturation and Hb saturation from each spectrum followed. Prior to MCR, all spectra were preprocessed with the second derivative, concatenation that allowed retention of specific parts of the visible and NIR wavelength regions, visible/NIR scaling, normalization, and mean centering.

Hb saturation and Mb saturation were measured separately in vivo. Hb saturation showed larger fluctuations with blood withdrawal and with blood re-infusion than did Mb saturation. This is expected since hemoglobin concentrations temporarily change a great deal with rapid blood withdrawals and infusions.

Arterial (pulsatile and non-pulsatile) and venous blood contribute to the Hb saturation measurement. Measurement of Hb saturation does not require pulsatile blood flow, as in pulse oximetry. Mb saturation is a measurement of the fraction of myoglobin that is bound to oxygen. Myoglobin is contained within muscle cells, and Mb saturation is an intracellular measure of oxygenation.

Although the specific exemplary embodiment described above is directed to a currently preferred embodiment wherein the oxygenation of muscle is calculated, it will be readily apparent to persons of skill in the art that the method may be extended according to the teachings in the present application to calculate the oxygenation of other tissues where there is no myoglobin, such as in the brain. In such applications rather than using the detected absorbance spectrum of muscle, the spectrum of a mixture of arterial, capillary, and venous hemoglobin could be analyzed generally using one or all of a suitably sculpted light sources, concatenated spectrum segments, spectral method to develop training data, and an LWR method to determine the oxygenation of the tissue that is not pulsatile arterial blood. Measurement of hemoglobin saturation using the present invention would not depend on the presence of a pulsatile signal, as pulse oximetry does.

While illustrative embodiments have been illustrated and described, it will be appreciated that various changes can be made therein without departing from the spirit and scope of the invention.

The embodiments of the invention in which an exclusive property or privilege is claimed are defined as follows:

1. A system for determining muscle oxygenation in a body, the system comprising:
   a probe comprising a housing having a housing face configured to abut the body;
   a processor connected to control a first light source operable to emit light at a first radiant flux in a visible wavelength range from a plurality of first emission locations on the housing face, and further connected to control a second light source operable to emit light at a second radiant flux in a near-infrared wavelength range from one or more second emission locations on the housing face such that the visible light emitted by the first light source and the near-infrared light emitted by the second light source are directed into the abutting body, wherein the first radiant flux is greater than the second radiant flux; and
   a light detector system configured to receive light from the body at a receiving location on the housing face and to transmit spectral information characterizing the received light to the processor;
   wherein the processor is configured to calculate a muscle oxygenation based on the spectral information transmitted by the light detector system; and further
   wherein the plurality of first emission locations and the one or more second emission locations are disposed along a circular arc centered on the receiving location.

2. The system of claim 1, wherein the receiving location is uniformly spaced from all of the plurality of first emission locations and the one or more second emission locations.

3. The system of claim 1, wherein the light detector system comprises a spectrometer, and further comprises an optical cable that transmits light from the receiving location on the abutting housing face to the spectrometer.

4. The system of claim 1, wherein the light detector system comprises a spectrophotometer operably configured to receive light from the receiving location on the housing face via a fiber optic cable.

5. The system of claim 1, wherein the visible wavelength range is within the range of 540-620 nm.

6. The system of claim 1, wherein the near-infrared wavelength range is within the range of 740-790 nm.

7. The system of claim 1, wherein the first radiant flux is produced by a plurality of light emitting diodes.

8. The system of claim 7, wherein the plurality of first emission locations on the housing face are disposed along a circular arc defining about one quarter of a circle centered on the receiving location.

9. The system of claim 1, wherein the first radiant flux is at least an order of magnitude greater than the second radiant flux.

10. The system of claim 1, wherein the first light source and the second light source are controlled to synchronously emit light simultaneously.

11. The system of claim 1, wherein the processor is configured to use the transmitted spectral information to calculate (i) a first sum of a concentration of oxymyoglobin and a concentration of oxyhemoglobin, (ii) a second sum of a concentration of deoxymyoglobin and a concentration of deoxyhemoglobin, and (iii) a muscle oxygenation based on the first sum and the second sum.

12. A system for detecting circulatory shock comprising:
   a probe comprising a housing having a housing face configured to abut a body;
   a processor connected to control a first light source operable to emit light at a first radiant flux in a visible wavelength range from a plurality of first emission locations on the housing face, and further connected to control a second light source operable to emit light at a second radiant flux in a near-infrared wavelength range from one or more second emission locations on the housing face such that the visible light emitted by the first light source and the near-infrared light emitted by the second light source are directed into the abutting body, wherein the first radiant flux is greater than the second radiant flux; and
   a light detector system configured to receive light from the body at a receiving location on the housing face and to transmit spectral information characterizing the received light to the processor;
   wherein the plurality of first emission locations and the one or more second emission locations are disposed along a circular arc centered on the receiving location; and further
   wherein the processor is configured to calculate a muscle oxygenation based on the spectral information transmitted by the light detector system, and to activate an alert if the calculated muscle oxygenation is below a predetermined threshold, thereby indicating a potential clinical concern for circulatory shock.

13. The system of claim 12, wherein the receiving location is uniformly spaced from all of the plurality of first emission locations and the one or more second emission locations.

14. The system of claim 12, wherein the light detector system comprises a spectrometer, and further comprising an optical cable that transmits light from the receiving location on the abutting housing face to the spectrometer.

15. The system of claim 12, wherein the light detector system comprises a spectrophotometer operably configured to receive light from the receiving location on the housing face via a fiber-optic cable.

16. The system of claim 12, wherein the visible wavelength range is within the range of 540-620 nm.

17. The system of claim 12, wherein the near-infrared wavelength range is within the range of 740-790 nm.

18. The system of claim 12, wherein the first radiant flux is produced by a plurality of light emitting diodes.

19. The system of claim 18, wherein the plurality of first emission locations are disposed along a circular arc defining about one quarter of a circle centered on the receiving location.

20. The system of claim 12, wherein the first radiant flux is at least an order of magnitude greater than the second radiant flux.

21. The system of claim 12, wherein the first light source and the second light source are controlled to synchronously emit light simultaneously.

* * * * *